United States Patent
Meyer et al.

(10) Patent No.: US 11,446,882 B2
(45) Date of Patent: Sep. 20, 2022

(54) SHAPED BONE FIBER-BASED PRODUCTS AND A METHOD OF MANUFACTURE THEREOF

(71) Applicant: Bacterin International, Inc., Belgrade, MT (US)

(72) Inventors: Todd Meyer, Bozeman, MT (US); Helena M. Lovick, N. Great Falls, MT (US); Michael Mansfield, Bozeman, MT (US); Daniel Cox, Bozeman, MT (US); Gregory Juda, Bozeman, MT (US)

(73) Assignee: Bacterin International, Inc., Belgrade, MT (US)

( * ) Notice: Subject to any disclaimer, the term of this patent is extended or adjusted under 35 U.S.C. 154(b) by 0 days.

(21) Appl. No.: 16/200,408

(22) Filed: Nov. 26, 2018

(65) Prior Publication Data

US 2019/0091942 A1    Mar. 28, 2019

Related U.S. Application Data

(62) Division of application No. 14/639,902, filed on Mar. 5, 2015, now Pat. No. 10,173,375.

(60) Provisional application No. 62/098,873, filed on Dec. 31, 2014, provisional application No. 61/948,442, filed on Mar. 5, 2014.

(51) Int. Cl.
| | |
|---|---|
| *B29C 67/24* | (2006.01) |
| *A61L 27/36* | (2006.01) |
| *A61L 27/06* | (2006.01) |
| *A61L 27/56* | (2006.01) |
| *B29L 31/00* | (2006.01) |

(52) U.S. Cl.
CPC .......... *B29C 67/24* (2013.01); *A61L 27/3608* (2013.01); *A61L 27/3683* (2013.01); *A61L 27/56* (2013.01); *A61L 2430/02* (2013.01); *A61L 2430/40* (2013.01); *B29L 2031/753* (2013.01); *D10B 2101/00* (2013.01); *Y10T 428/26* (2015.01)

(58) Field of Classification Search
CPC .................................................. A61L 27/3608
See application file for complete search history.

(56) References Cited

U.S. PATENT DOCUMENTS

| | | |
|---|---|---|
| 5,314,476 A | 5/1994 | Prewett et al. |
| 5,507,813 A | 4/1996 | Dowd et al. |
| 5,513,662 A | 5/1996 | Morse et al. |
| 6,124,273 A | 9/2000 | Drohan et al. |
| 6,395,311 B2 | 5/2002 | Qi |
| 6,436,138 B1 | 8/2002 | Dowd et al. |

(Continued)

FOREIGN PATENT DOCUMENTS

| | | |
|---|---|---|
| WO | WO 2014/110537 | 7/2014 |
| WO | WO 2014/151091 | 9/2014 |

OTHER PUBLICATIONS

Claes et al. "Fracture healing under healthy and inflammatory conditions," Nature Reviews Rheumatology, Mar. 2012, vol. 8, pp. 133-143.

(Continued)

*Primary Examiner* — Alexandre F Ferre
(74) *Attorney, Agent, or Firm* — Sheridan Ross P.C.

(57) ABSTRACT

The present invention relates to shaped, bone fiber-based products and methods to make the same.

18 Claims, 7 Drawing Sheets

(56) References Cited

U.S. PATENT DOCUMENTS

| | | | |
|---|---|---|---|
| 6,541,024 B1 | 4/2003 | Kadiyala et al. | |
| 6,620,196 B1 | 9/2003 | Trieu | |
| 6,808,585 B2 | 10/2004 | Boyce et al. | |
| 7,312,301 B2 | 12/2007 | Fang et al. | |
| 7,323,193 B2 | 1/2008 | Morris et al. | |
| 7,582,309 B2 | 9/2009 | Rosenbert et al. | |
| 7,726,002 B2 | 6/2010 | Shimp et al. | |
| 8,133,421 B2 | 3/2012 | Boyce et al. | |
| 8,574,825 B2 | 11/2013 | Shelby et al. | |
| 8,859,007 B2 | 10/2014 | Carter et al. | |
| 8,980,248 B2 | 3/2015 | Shoichet et al. | |
| 9,114,191 B2 | 8/2015 | Shelby et al. | |
| 9,168,138 B2 | 10/2015 | O'Neil et al. | |
| 9,675,645 B2 | 6/2017 | Wei | |
| 10,173,375 B2 | 1/2019 | Meyer et al. | |
| 2002/0192263 A1 | 12/2002 | Merboth et al. | |
| 2004/0024457 A1* | 2/2004 | Boyce | A61F 2/08 623/13.17 |
| 2004/0034434 A1 | 2/2004 | Evans et al. | |
| 2004/0210310 A1 | 10/2004 | Trieu | |
| 2004/0249461 A1 | 12/2004 | Ferree | |
| 2004/0258732 A1 | 12/2004 | Shikinami | |
| 2005/0004242 A1 | 1/2005 | Sotome et al. | |
| 2006/0015184 A1 | 1/2006 | Winterbottom et al. | |
| 2006/0030948 A1 | 2/2006 | Manrique et al. | |
| 2007/0160622 A1 | 7/2007 | Turnell et al. | |
| 2007/0179607 A1 | 8/2007 | Hodorek et al. | |
| 2008/0091270 A1 | 4/2008 | Miller et al. | |
| 2009/0028957 A1 | 1/2009 | Daniloff | |
| 2010/0036503 A1 | 2/2010 | Chen et al. | |
| 2010/0204699 A1 | 8/2010 | Wei et al. | |
| 2010/0331257 A1 | 12/2010 | Bayon et al. | |
| 2011/0097374 A1* | 4/2011 | Serhan | A61K 38/1875 424/423 |
| 2012/0010728 A1 | 1/2012 | Sun et al. | |
| 2013/0136777 A1 | 5/2013 | Behnam et al. | |
| 2013/0190875 A1 | 7/2013 | Shulock et al. | |
| 2013/0345826 A1 | 12/2013 | Li et al. | |
| 2014/0052247 A1 | 2/2014 | Daniel et al. | |
| 2014/0142041 A1 | 5/2014 | Koob | |
| 2014/0257516 A1 | 9/2014 | Mills et al. | |
| 2014/0277577 A1 | 9/2014 | Garigapati | |
| 2014/0314822 A1 | 10/2014 | Carter et al. | |
| 2015/0004414 A1 | 1/2015 | Ogura et al. | |
| 2015/0093429 A1 | 4/2015 | Carter et al. | |
| 2016/0287747 A1 | 10/2016 | Schallenberger | |
| 2017/0000624 A1 | 1/2017 | Schallenberger et al. | |

OTHER PUBLICATIONS

Pietrzak et al., "BMP depletion occurs during prolonged acid demineralization of bone: characterization and implications for graft preparation," Cell and Tissue Banking, 2011, vol. 12(2), pp. 81-88.

Simmonds et al. "Safety and Effectiveness of Recombinant Human Bone Morphogenetic Protein-2 for Spinal Fusion," Annals of Internal Medicine, Jun. 2013, vol. 158, No. 12, pp. 877-889.

Official Action for U.S. Appl. No. 14/639,902, dated Aug. 25, 2016, 9 pages.

Final Action for U.S. Appl. No. 14/639,902, dated Mar. 28, 2017 10 pages.

Official Action for U.S. Appl. No. 14/639,902, dated Oct. 5, 2017 10 pages.

Official Action for U.S. Appl. No. 14/639,902, dated Apr. 10, 2018 9 pages.

Notice of Allowance for U.S. Appl. No. 14/639,902, dated Aug. 29, 2018 6 pages.

Notice of Allowability for U.S. Appl. No. 14/639,902, dated Sep. 12, 2018, 3 pages.

Official Action for U.S. Appl. No. 15/087,553, dated Jun. 29, 2018 7 pages Restriction Requirement.

Official Action for U.S. Appl. No. 15/087,553, dated Oct. 31, 2018 13 pages.

Official Action for U.S. Appl. No. 15/199,458, dated Jul. 26, 2018 Restriction Requirement.

Official Action for U.S. Appl. No. 15/199,458, dated Nov. 28, 2018, 9 pages.

Official Action for U.S. Appl. No. 15/397,619, dated Mar. 24, 2017 9 pages Restriction Requirement.

Official Action for U.S. Appl. No. 15/397,619, dated Oct. 19, 2017 17 pages.

Official Action for U.S. Appl. No. 15/199,458, dated Apr. 17, 2019, 8 pages.

Official Action for U.S. Appl. No. 15/199,458, dated Nov. 18, 2019, 9 pages.

\* cited by examiner

Rehydrated product lyophilized in accordance with the existing art

Rehydrated product formed by the method of the present invention

SHAPED BONE FIBER-BASED PRODUCTS AND A METHOD OF MANUFACTURE THEREOF

CROSS REFERENCE TO RELATED APPLICATIONS

This application is a divisional of U.S. patent application Ser. No. 14/639,902, filed on Mar. 5, 2015, which claims priority under 35 U.S.C. § 119(e) to U.S. Provisional Patent Application Ser. No. 61/948,442 filed Mar. 5, 2014, and U.S. Provisional Patent Application Ser. No. 62/098,873 filed on Dec. 31, 2014. Each of these references are incorporated herein in their entirety by reference.

FIELD OF THE INVENTION

The present embodiments generally relate to shaped bone fiber-based products and a method of manufacturing thereof.

DESCRIPTION OF THE PRIOR ART

Methods for manufacturing shaped, bone fiber-based products are known in the prior art. The majority of these methods require the use of excipients, carriers and/or specialized drying conditions (pressure, lyophilization, etc.) to generate products of the desired shape and physical properties. A need remains for a facile method of generating shaped, fiber-based products with adequate physical properties of mold release, flexibility, compressibility, cohesion, and pliability post-shaping.

U.S. Pat. No. 5,314,476 to Prewett et al. (incorporated in its entirety by reference) discloses demineralized bone particles with a median length:median thickness of 10:1 incorporated into an osteogenic composition. The osteogenic composition maintains its cohesiveness and resists erosion subsequent to being applied to an osseous defect. The composition contains between about 20-80 wt. % of a carrier (e.g., glycerol) and describes producing particles of 10 mm length by 0.5 mm thick which are demineralized, and mixed with particles with glycerol to a putty-like consistency.

U.S. Pat. No. 5,507,813 to Dowd et al. (incorporated in its entirety by reference) discloses the production of sheets from elongate bone particles, especially demineralized bone particles. The sheets comprise at least 60 wt. % bone particles of lengths of 10-100 mm, thicknesses of 0.02-1 mm, and widths of 2-5 mm. Dowd describes a method of production of the sheet using demineralized particles by spreading wet particles on a screen, applying a force (8 psi) while drying in an oven, and then cutting the sheet to size.

U.S. Pat. No. 6,436,138 to Dowd et al. (Dowd II) discloses a process for fabricating shaped material from demineralized bone particles similar to the process disclosed in Dowd. However, the oven-drying step is altered to finish with lyophilization prior to warming. The product may be formed in a desired shape or the sheet of particles may be positioned on a mold support.

U.S. Pat. No. 6,808,585 to Boyce et al. discloses an osteogenic osteoimplant in the form of a flexible sheet, which has a void volume that is not greater than about 32%. The method to make the product comprises providing a coherent mass of bone-derived particles, then mechanically shaping the mass of particles to form a flexible sheet. The bone particles are demineralized, lyophilized, and then mixed with a biocompatible carrier (50% by weight glycerol/water), then the mass is compressively contacted by hand (rolled out) into a sheet of minimal thickness. The products of Boyce compared to Dowd supposedly had more void volume, less % demineralized bone matrix (DBM), greater elasticity (less ability to maintain shape).

U.S. Pat. No. 8,133,421 to Boyce et al. (Boyce II) discloses a method of making an implant comprised of an aggregate of bone particles and optional reinforces, where at least some of the bone particles are not fully demineralized. The aggregate is shaped into a coherent mass with a bulk density of greater than approximately 0.7 g/cm$^3$.

U.S. Pat. No. 7,582,309 to Rosenberg et al. discloses a DBM composition of fibers with lengths between 250 µm to 2 mm and a biocompatible liquid to form a coherent, formable mass. The fibers are present in an amount greater than 40 wt % of dry component.

U.S. Pat. No. 7,323,193 to Morris et al discloses a process to demineralize whole bone and thereafter subdividing the bone into particles by applying pressure to the bone with a mechanical press. The pressure is applied from about 1000 to 40000 psi.

U.S. Patent Publication No. 2006/0030948 to Manrique et al. discloses an osteoimplant where demineralized bone particles are mechanically entangled with each other and are then shaped in a mold.

U.S. Patent Publication No. 2013/0136777 to Behnam et al. discloses osteoinductive compositions comprising partially demineralized bone where the collagen structure is disrupted.

The present invention discloses products and methods that are advantageous over this art as discussed below.

SUMMARY OF THE INVENTION

The disclosed invention is directed to a shaped fiber-based product and a method of manufacturing thereof. The shaped fiber-based product consists of a three-dimensional form of dimensions established by the use of a mold. The properties of the shaped fiber-based product provide improved self-adhesion, flexibility and compressibility over related products in the prior art. The method of manufacturing relies on judicious selection of fiber shapes and sizes, hydration with a water-miscible, low boiling solvent, molding, and drying of the shaped, fiber-based product. In some embodiments, the water-miscible, low boiling solvent may be used in combination with water and/or a water-based solution. Fibers for the product may be cut from bone, foodstuffs, wood, plant-based materials, elastomers, thermoplastics, but are preferably cut from bone. In some embodiments, the fibers may be exposed to drying or lyophilization conditions. In some embodiments, demineralized bone fibers are shaped and sized to specific dimensions to enhance entanglement and subsequent final product self-adhesion, flexibility, and compressibility.

Another aspect of the invention is the use of a controlled drying/lyophilization cycle following fiber molding to provide a product with enhanced cohesiveness and flexibility. A further aspect of the method is the use of a water-miscible, low boiling solvent prior the final drying of the fiber-based articles to provide improved fiber entanglement, fiber shaping, final product shape retention, and mold release of the final product. The use of a water-miscible, low boiling solvent further enhances the desired final product properties of self-adhesion, flexibility, and compressibility.

An aspect of the invention is a shaped, bone fiber-based product of specific dimensions. The product includes a plurality of bone fibers, where the average length of the fibers is between about 1 to about 200 mm, and where the product is within between about 60% to about 100% of at least one of a pre-dehydrated property upon rehydration. The pre-dehydrated property can be shape, flexibility, or compressibility.

The product may be a cube, a block, a strip, or a sphere. The residual moisture content of the product may be less than about 6%. The rehydrated product may be compressible to about 80% of an original size of the rehydrated product before dehydration. In some embodiments, following compression the rehydrated product substantially returns its original shape of the product before dehydration. In some embodiments, the rehydrated product remains greater than about 90% intact following rehydration compared to its intact percentage before dehydration. The rehydrated product may remain greater than about 90% intact after it is bent, compressed, twisted, squeezed or rolled. The rehydrated product may be bendable to about 90°. The rehydrated product may be osteoinductive. The rehydrated product may maintain at least one property, where the property is shape, cohesiveness, pliability, or compressibility, for at least one year after rehydration. The void to fiber ratio of the product may be between about 1:99 to about 1:11.

The fibers may be cortical bone, cancellous bone, or combinations thereof. In some embodiments, the fibers may be fully demineralized, partially demineralized, mineralized or any combinations thereof. The fibers may be partially dehydrated, fully dehydrated, or fully hydrated. The fibers may be allogeneic, autogeneic, and xenogeneic tissues, and combinations thereof. The fibers may have a diameter of between about 0.1 mm to about 30 mm. The fibers may be cut from a bone in a direction about 15° to about 90° from the grain of the native collagen fibers.

The product may rehydrate in at least one aqueous liquid, and may rehydrate within about 15 seconds. The aqueous liquid may be water, saline, buffer, balanced salt solution, blood, bone marrow aspirate, plasma, or combinations thereof.

An aspect of the invention is a method for forming a shaped, bone fiber-based product of specific dimensions. The method includes cutting bone into fibers, entangling the bone fibers in an aqueous solution, placing the entangled fibers into a mold and drying the fibers in the mold while warming under reduced pressure.

The product may be a cube, a block, a strip, or a sphere. The residual moisture content of the product may be less than about 6%. The rehydrated product may be compressible to about 80% of an original size of the rehydrated product before dehydration. In some embodiments, following compression the rehydrated product substantially returns its original shape of the product before dehydration. In some embodiments, the rehydrated product remains greater than about 90% intact following rehydration compared to its intact percentage before dehydration. The rehydrated product may remain greater than about 90% intact after it is bent, compressed, twisted, squeezed or rolled. The rehydrated product may be bendable to about 90°. The rehydrated product may be osteoinductive. The rehydrated product may maintain at least one property, where the property is shape, cohesiveness, pliability, or compressibility, for at least one year after rehydration. The void to fiber ratio of the product may be between about 1:99 to about 1:11.

The fibers may be cortical bone, cancellous bone, or combinations thereof. In some embodiments, the fibers may be fully demineralized, partially demineralized, mineralized or any combinations thereof. The fibers may be partially dehydrated, fully dehydrated, or fully hydrated. The fibers may be allogeneic, autogeneic, and xenogeneic tissues, and combinations thereof. The fibers may have a diameter of between about 0.1 mm to about 30 mm. The fibers may be cut from a bone in a direction about 15° to about 90° from the grain of the native collagen fibers.

The mold may be made from ceramic, aluminum, stainless steel, other metals, and combinations thereof. The mold may have at least one opening that may be a gap, a perforation, a screen, a slit, a shape and combinations of openings. The mold may be capable of withstanding steam sterilization. The mold may have variable dimensions, which may be determined by an assessment of the void to be filled in the patient. The mold may include a lid, which may be attached to the mold or detached from the mold.

The drying or dehydration step may be lyophilization. In some embodiments, the drying or dehydration step may include heating the mold to a temperature between about 30° C. to about 80° C. The dehydration or drying step may include heating the mold under reduced pressure of between about 1 nTorr to about 740 Torr. In some embodiments, the drying or dehydration step may take place with airflow through the mold.

An aspect of the invention is a three-dimensional shape fiber-based product of specific dimensions. The product includes a plurality of fibers, with an average length between about 1 mm to about 200 mm. The material for the fibers is bone, wood, food stuffs, plant-based materials, elastomers, thermoplastics, or combinations thereof.

The product may be a cube, a block, a strip, or a sphere. The residual moisture content of the product may be less than about 6%. The rehydrated product may be compressible to about 80% of an original size of the rehydrated product before dehydration. In some embodiments, following compression the rehydrated product substantially returns its original shape of the product before dehydration. In some embodiments, the rehydrated product remains greater than about 90% intact following rehydration compared to its intact percentage before dehydration. The rehydrated product may remain greater than about 90% intact after it is bent, compressed, twisted, squeezed or rolled. The rehydrated product may be bendable to about 90°. The rehydrated product may be osteoinductive. The rehydrated product may maintain at least one property, where the property is shape, cohesiveness, pliability, or compressibility, for at least one year after rehydration. The void to fiber ratio of the product may be between about 1:99 to about 1:11.

The fibers may be cortical bone, cancellous bone, or combinations thereof. In some embodiments, the fibers may be fully demineralized, partially demineralized, mineralized or any combinations thereof. The fibers may be partially dehydrated, fully dehydrated, or fully hydrated. The fibers may be allogeneic, autogeneic, and xenogeneic tissues, and combinations thereof. The fibers may have a diameter of between about 0.1 mm to about 30 mm. The fibers may be cut from a bone in a direction about 15° to about 90° from the grain of the native collagen fibers.

The product may rehydrate in at least one aqueous liquid, and may rehydrate within about 15 seconds. The aqueous liquid may be water, saline, buffer, balanced salt solution, blood, bone marrow aspirate, plasma, or combinations thereof.

An aspect of the invention is a method of forming a three-dimensional shape fiber-based product of specific dimensions. The method includes contacting a plurality of fibers with a solvent. The solvent is water miscible, low boiling solvent. The fibers are then placed into a mold and dehydrated to form the product.

The product may be a cube, a block, a strip, or a sphere. The residual moisture content of the product may be less than about 6%. The rehydrated product may be compressible to about 80% of an original size of the rehydrated product before dehydration. In some embodiments, following compression the rehydrated product returns its original shape of the product before dehydration. In some embodiments, the rehydrated product remains greater than about 90% intact following rehydration compared to its intact percentage before dehydration. The rehydrated product may remain greater than about 90% intact after it is bent, compressed, twisted, squeezed or rolled. The rehydrated product may be bendable to about 90°. The rehydrated product may be osteoinductive. The rehydrated product may maintain at least one property, where the property is shape, cohesiveness, pliability, or compressibility, for at least one year after rehydration. The void to fiber ratio of the product may be between about 1:99 to about 1:11.

The solvent mixture may include water and the water miscible, low boiling solvent. In some embodiments, the solvent may include a water-based solution and the water miscible, low boiling solvent. The water-based solution may be an aqueous acid, an aqueous base, a balanced salt solution, a buffer, or combinations thereof. In some embodiments, the ratio of the water-based solution is mixed with the water miscible, low boiling solvent may be between about 1:99 to about 99:1. The water may be mixed with the water miscible, low boiling solvent in a ratio of about 1:99 to about 99:1. The water miscible, low boiling solvent may be acetone, acetonitrile, ethanol, methanol, tetrahydrofuran, or combinations thereof. In some embodiments, the water miscible, low boiling solvent may be ethanol. In some embodiments, the fibers may be contacted with ethanol and water. In some embodiments, the fibers may be contacted with the solvent prior to or after placement in the mold.

When the fibers contact the water miscible, low boiling solvent, the fiber curl, fiber twist, and/or fiber entanglement may increase.

The material for the fibers may be bone, wood, foodstuff, plant-based material, an elastomer, a thermoplastic, or a combination thereof. If the material is bone, then the bone may be cortical bone, cancellous bone, or combinations thereof. The bone may be demineralized, partially dehydrated, or completely hydrated.

The mold may be made from ceramic, aluminum, stainless steel, other metals, and combinations thereof. The mold may have at least one opening that may be a gap, a perforation, a screen, a slit, a shape and combinations of openings. The mold may be capable of withstanding steam sterilization. The mold may have variable dimensions, which may be determined by an assessment of the void to be filled in the patient. The mold may include a lid, which may be attached to the mold or detached from the mold.

The drying or dehydration step may be lyophilization. In some embodiments, the drying or dehydration step may include heating the mold to a temperature between about 30° C. to about 80° C. The dehydration or drying step may include heating the mold under reduced pressure of between about 1 nTorr to about 740 Torr. In some embodiments, the drying or dehydration step may take place with airflow through the mold.

BRIEF DESCRIPTION OF THE FIGURES

FIG. 7a illustrates the effect of acid exposure on BMP-2. FIG. 7b illustrates the effect of acid exposure on BMP-4. FIG. 7c illustrates the effect of acid exposure on BMP-7. Sample A represents the growth factor content of demineralized cancellous bone matrix processed according to a preferred embodiment of the present invention, showing higher levels of BMPs versus samples B and C. Sample B represents the growth factor content of demineralized cancellous bone matrix processed according to methods currently being practiced in the industry, showing reduced levels of BMPs in comparison with sample A representing the current invention. Sample C represents the growth factor content in demineralized cancellous bone matrix processed by exposure to acid for 24 hours, demonstrating damage or removal of BMPs.

DETAILED DESCRIPTION OF THE INVENTION

Figure 1:
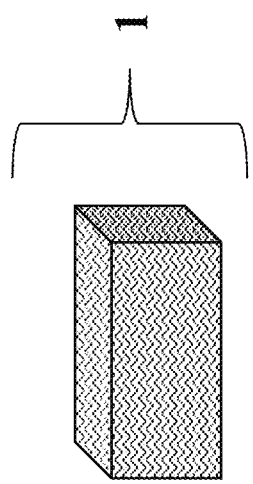
FIG. 1 illustrates a perspective graphical view of a shaped fiber-based product manufactured by the method of the present invention.

The present invention relates to a shaped bone fiber-based product and methods of making the same.

"Allogeneic" or "allograft", as used herein, refers to tissue derived from a non-identical donor of the same species, which may be a DBM.

"Autogeneic" or "autograft", as used herein, refers to tissue derived from and implanted into the same identical patient.

"Biocompatible", as used herein, refers to the property of being biologically compatible with a living being by not causing harm.

"Osteoinductive", as used herein, refers to the ability of a material to induce bone healing via recruitment of osteoprogenitor cells.

"Patient", as used herein, refers to a living recipient of the biomaterial-based implants of the present invention.

"Xenogeneic" or "xenograft", as used herein, is defined as tissue derived from a non-identical donor of a different species.

The shaped fiber-based products of the invention have many advantages over the prior art. The rehydrated fiber-based products of the invention compress under a force of between about 10 g-force/square cm to about 4000 g-force/square cm. The rehydrated, shaped fiber-based product may be compressible to about 80% of its original size, to about 60% of its original size, to about 20% of its original size, to about 5% of its original size without loss of structural integrity or fiber cohesion. Upon removal of an external compressing force, the products return to their original shape. The shaped fiber-based product may also rehydrate rapidly within an aqueous fluid over a period of about 15 seconds to about 30 minutes, of about 1 minute to about 25 minutes, or of about 5 minutes to about 20 minutes. In some embodiments, the shaped fiber-based product may also have a high rehydration rate of between about 0.5 mL of liquid/g of product/minute to about 10 mL of liquid/g of product/minute. Suitable aqueous fluids include, but are not limited to, water, saline, buffer, balanced salt solution, blood, bone marrow aspirate, plasma and combinations thereof.

The shaped product is not a putty, but rather a sponge-like material may be composed of a single material or a mixture of materials which may be used as scaffolding during bone regrowth. In some embodiments, the shaped product may be composed of solely bone tissue. Furthermore, while the invention may be used to produce a sheet that may later be cut to form a specific shape, the invention allows for the shape to be formed without this additional step of cutting. The base material of the invention is fibers rather than particles, for example bone fibers rather than bone particles. Furthermore, the fiber to void ratio may be determined and maintained because an external force is not required during the formation of the shaped fiber base product of the present invention.

Utilizing the drying/lyophilization parameters of the invention, the final shape of the product is within about 10% of its projected size based on the mold. Finally, the void to fiber ratio may be controlled to between about 1:99 to about 1:1, with a preferred void to fiber ratio ranging from about 1:19 to about 1:3. In some embodiments, the void to fiber ratio may be between about 1:99 to about 1:11, about 1:75 to about 1:4, between about 1:25 to about 1:5, between about 1:20 to about 1:6, or between about 1:10 to about 1:5.

In some embodiments, the method for making the shaped fiber-based product utilizes low boiling solvents to facilitate final drying of the fiber-based material via azeotropic drying. The method for making the shaped fiber-based product also advantageously releases the final product from a mold with minimal if any damage or breakage. Furthermore, because of the advantageous mold release, the shape of the shaped fiber-based product is retained after removal. Thus, the final shape is within about 10% of its projected size based on the mold. Finally, the fiber to void ratio may be controlled to between about 1:99 to about 1:1, with a preferred void to fiber ratio ranging from about 1:19 to about 1:3. In some embodiments, the void to fiber ratio may be between about 1:99 to about 1:11, about 1:75 to about 1:4, between about 1:25 to about 1:5, between about 1:20 to about 1:6, or between about 1:10 to about 1:5.

Figure 2:
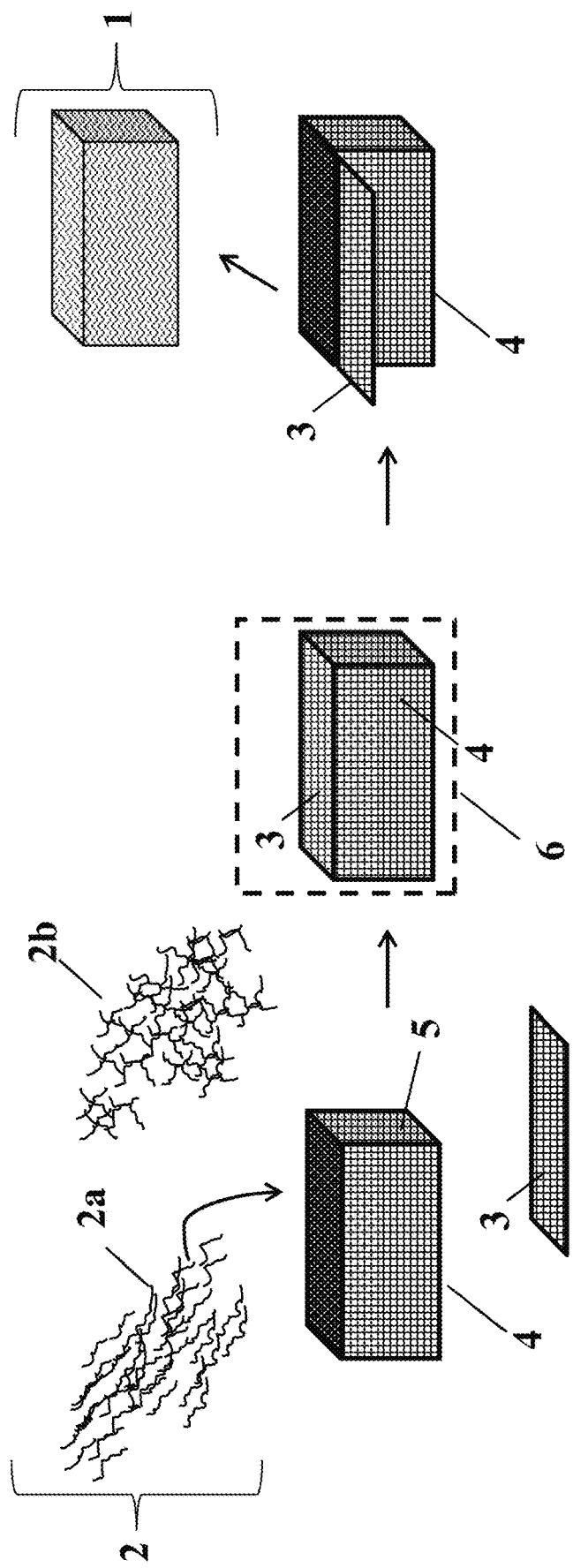
FIG. 2 illustrates a perspective graphical view of the method of form a shaped fiber-based product in accordance with the present invention.

FIG. 1 illustrates a perspective graphical view of a shaped fiber-based product 1 formed by the method of this invention. The shaped fiber-based product may be shaped in the form of a block as shown, or in the form of a cube, strip, sphere, or other three-dimensional shape as desired. The shape of the product may be uniform or irregular as desired by the end-user of the article. In some embodiments, the size of the product may be larger than the final desired product and cut to a desired dimension. As illustrated in FIG. 2, the fiber-based material of the product may be formed from fiber components in a regular 2a or irregular arrangement 2b. In some embodiments, the fibers may be placed in a consistent, parallel orientation 2a. In some embodiments, the fibers of the product may be entangled and interlaced in multiple orientations 2b to provide strength and adhesion of the fibers to one another within the resultant product. In some embodiments, the shaped product 1 may contain voids within the fiber-based material. The void to fiber ratios may vary from about 1:99 to about 1:1, with a preferred void to fiber ratio ranging from about 1:19 to about 1:3. In some embodiments, the void to fiber ratio may be between about 1:99 to about 1:11, about 1:75 to about 1:4, between about 1:25 to about 1:5, between about 1:20 to about 1:6, or between about 1:10 to about 1:5.

Figure 6:
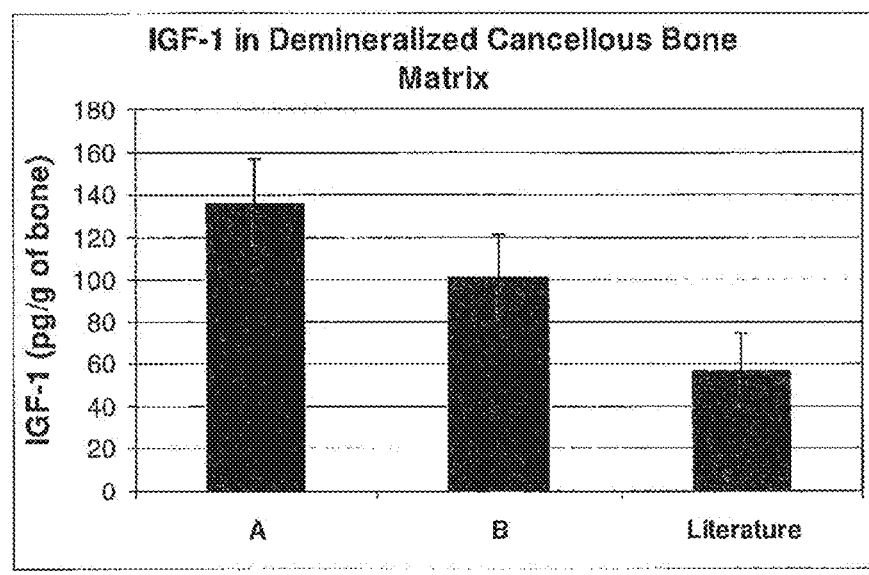
FIG. 6 is a chart, which represents levels of insulin-like growth factor-1 (IGF-1) in three samples of demineralized cancellous bone matrix from the same donor after subjecting the three samples to different demineralization protocols. Samples A and B represent demineralized cancellous bone matrix produced according to the processes, methodologies, and techniques of the present invention. Sample C represents demineralized cancellous bone matrix produced according to the state of the prior art found in the literature, demonstrating damage or removal of IGF-1.
Figures 7A, 7B, 7C:
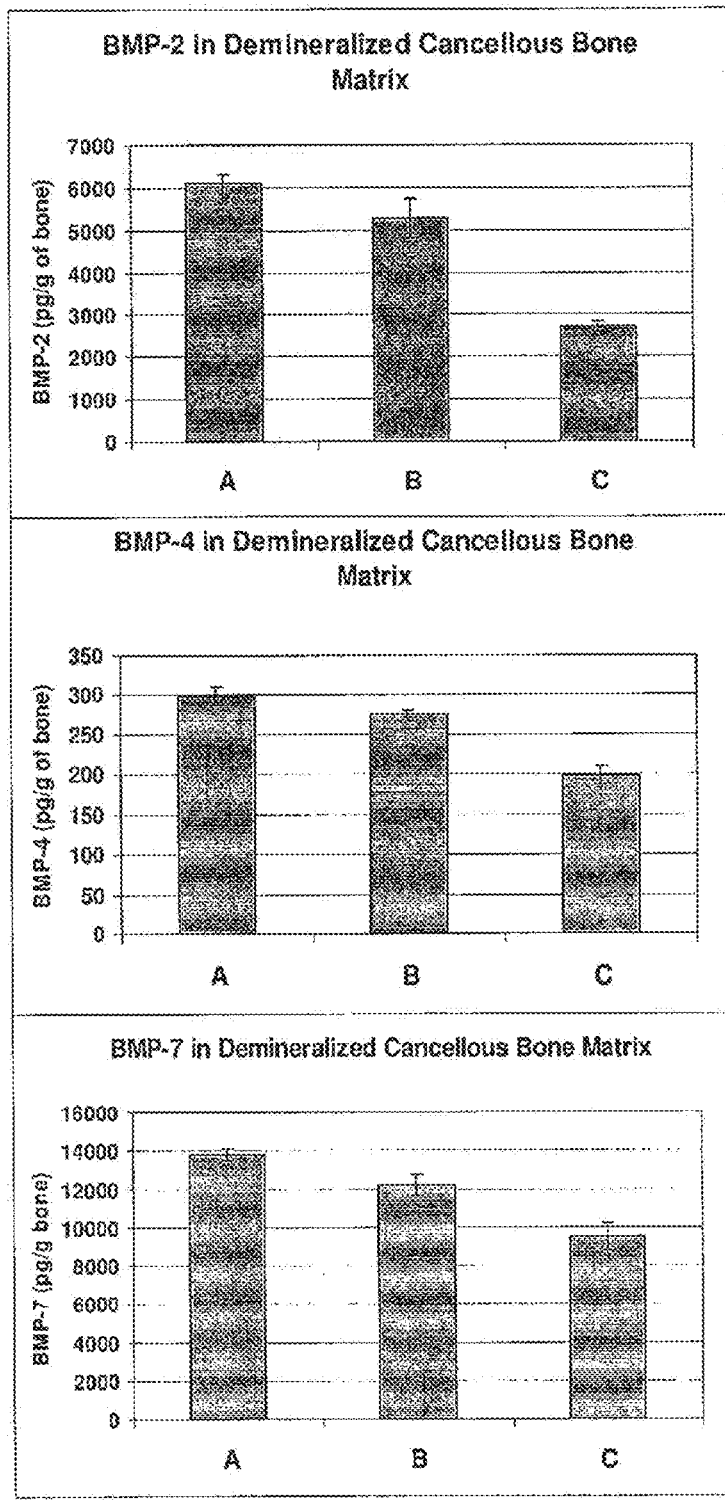
FIGS. 7a-7c illustrate the effect of acid exposure on the levels of native growth factors in demineralized cancellous bone.

The fibers that comprise the shaped product 1 may consist of bone, wood, food stuffs, plant-based materials, elastomers, thermoplastics, or combinations thereof. These fibers may be fully or partially solvated as needed to form a product of the desired moisture level and physical properties. The fibers within the shaped product 1 may be of lengths of about 1 mm to about 200 mm, of about 2 mm to about 150 mm, of about 5 mm to about 70 mm, to about 10 mm to about 60 mm. The average length of the fibers may be between about 15 mm to about 50 mm, in some embodiments about 30 mm. The fibers may have a width or diameter of about 0.1 mm to about 30 mm, of about 0.2 mm to about 15 mm, of about 0.5 mm to about 10 mm, to about 1 mm to about 8 mm. The average width or diameter may be between about 1 mm to about 5 mm, in some embodiments between about 2-3 mm. The thickness of the shaped product may be between about 0.01 mm to about 1 mm. In some embodiments, the thickness may be about 0.01 mm, about 0.05 mm, about 0.1 mm, about 0.2 mm, about 0.25 mm, about 0.3 mm, about 0.4 mm, about 0.5 mm, about 0.6 mm, about 0.7 mm, about 0.8 mm, about 0.9 mm, about 0.95 or about 1 mm. The shaped product 1 is composed of bone fibers, the bone may be cortical, cancellous, or a combination of the two bone types. The bone may be allogeneic, autogeneic, or xenogeneic. In some embodiments, other materials may be entangled within or added to the fibers (e.g., bone chips, biocompatible minerals, and BioGlass). The bone fibers for the invention may be generated by a variety of methods and techniques known in the prior art, for example U.S. Pat. No. 5,314,476, which is incorporated in its entirety by reference. In some embodiments, the bone is cut into fibers in an angle to the plane of the native collagen fibers within the bone, wherein the cutting blade is at an angle of about 30° to 90°, of about 45° to 90°, or of about 60° to 90°. The fibers comprising the shaped product 1 may be mineralized, fully demineralized, partially demineralized, or a combination of the foregoing. Demineralized bone matrix for use by the disclosed method may be prepared using any method or techniques known in the art, for a typical demineralization protocol. Example demineralization protocols are disclosed in U.S. Pat. No. 5,314,476, or 8,574,825, each reference is incorporated by reference in their entirety. In some embodiments, the demineralization protocol for the bone fibers may be optimized based on the bone fiber type to provide the maximum level of growth factors, such as bone morphogenetic proteins (BMPs). FIG. 6 illustrates an IGF-1 concentration of greater than 60 pg of IGF per gram of demineralized bone matrix. FIG. 7a illustrates a BMP-2 concentration of greater than 2700 pg of BMP-2 per gram of demineralized bone matrix. FIG. 7b illustrates a BMP-4 concentration of greater than 200 pg of BMP-4 per gram of demineralized bone matrix. FIG. 7c illustrates a BMP-2 concentration of greater than 9000 pg of BMP-7 per gram of demineralized bone matrix. Following any necessary pre-treatment (e.g., demineralization), the fibers 2 may be contacted with a water miscible, low boiling solvent. In some embodiments, the water miscible, low boiling solvent may be used in combination with water and/or water-based solutions (e.g., buffers). The contact method for the fibers 2 and the solvent may consist of pouring the solvent over the fibers, soaking the fibers in the solvent, forming a slurry of the fibers in the solvent, or a combination of these contact methods. In some embodiments, the ratio of solvent volume to mass of the fibers may be selected from a range of about 0.5 mL of solvent/gram of fibers to about 30 mL solvent/gram of fibers, from about 1 mL of solvent/gram of fibers to about 20 mL solvent/gram of fibers. Judicious selection of the solvent volume to mass of the fibers allows tuning of the void to fiber ratio within the final fiber-based material. In some embodiments, the demineralized bone fibers may have a residual calcium level of less than about 8%, less than about 6%, or less than about 2%. Suitable water miscible, low boiling solvents include, but are not limited to, acetone, acetonitrile, ethanol, methanol, tetrahydrofuran, and combinations thereof. In some embodiments, the water miscible, low boiling solvents from a low boiling azeotrope with water to facilitate final product drying. Suitable water-based solutions included, but are not limited to, aqueous acids, aqueous bases, balanced salt solutions, and buffers. Suitable aqueous acids include, but are not limited to, acetic acid, ascorbic acid, hydrochloric acid, citric acid, sulfuric acid, formic acid, succinic acid, and lactic acid. The concentration of the aqueous acids may range from 0.01 to 10 M. Suitable aqueous bases include, but are not limited to, hydroxides, carbonates, phosphate, and ammonia. The concentration of the aqueous bases may range from about 0.01 to about 10M. Counter ions of the aqueous bases include, but are not limited to, sodium, potassium, calcium, and ammonium. Suitable balanced salt solutions and buffers include, Hank's balanced salt solution, phosphate buffered saline, and saline.

A method of forming the shaped fiber-based products 1 may consist of placing the fibers 2, into contact with a water miscible, low boiling solvent. By contacting the fibers with a water miscible, low boiling solvent, the fibers may become further curled, twisted, shriveled, or a combination thereof. The increased curling, twisting, and/or shriveling of the fibers by a water miscible, low boiling solvent promotes fiber entanglement and subsequent shape retention of the final product. The fibers thus contacted with solvent are then placed within a mold 4 as shown in FIG. 2. Following any necessary pre-treatment (e.g., demineralization), the fibers 2 may be placed within a mold 4 as illustrated in FIG. 2. The mold 4 is capable of forming a three-dimensional shape. In some embodiments, the mold may fully enclose the fibers, or may have a lid 3 if desired. The lid 3 may be attached to the mold, detachable, or separate from the mold. The mold 4 and lid 3 may be perforated to fully or partially to allow removal of moisture from the fibers 2 during shaping. In other embodiments, the mold may be used to form a three-dimensional shape, for example a sheet of material, which may be further shaped. The mold 4 may be composed of various heat resistant materials such as, but not limited to, ceramics, elastomers, aluminum, stainless steel, thermoplastics, any other metals, or combinations thereof. The mold 4 may be amenable to steam sterilization. The mold 4 dimensions may be pre-set or adjustable to the desired final product dimensions. The mold 4 may be constructed of a screen-like material. The mold 4 may have a non-stick coating, such as Teflon. The mold 4 or mold lid 3 may apply adjustable inward pressure.

In some embodiments, the mold 4 may have drainage holes or openings to allow moisture to enter and exit the product during use. In some embodiments, the mold 4 may have openings or drainage holes at least on one side 5. In another embodiment, the mold may be comprised of only three sides so that moisture may exit from open sides of the mold 4. In another embodiment, the mold 4 may be composed of a screen with numerous openings to allow moisture entry or exit during use. In other embodiments, the mold 4 may be a sieve or strainer.

The shaped product 1 may be shaped specifically to fill a void. The void may be determined by pre-assessment of a void, such as a bone void within a patient. The final use of the shaped product 1 may be placement within a void of the patient.

During the forming of the shaped product 1, the fibers may be laid in a regular pattern 2a within the mold 4, or entangled as a mesh, braid, or interwoven in some manner 2b prior to placement within the mold 4. In some embodiments, the fibers may be laid or entangled around another article. If the fibers are placed around another article, the contained article may be composed of the same material or of materials of a different composition than the surrounding fibers (e.g., a shaped fiber-based article composed of demineralized cancellous fibers may be placed inside fibers composed of demineralized cortical bone). The contained article may be composed of elastomers, ceramics, metals, metal alloys, or plastics.

The fibers 2 are contacted with a solution containing a water miscible, low boiling solvent prior to placement or after placement in the mold 4. The solution containing a water miscible, low boiling solvent, the filled mold may be held at temperatures ranging from about −10° C. to about 70° C.; preferably, the solution will be used at room temperature. In some embodiments, the fibers may be contacted with a combination of water and a water miscible, low boiling solvent prior to placement or after placement in the mold 4. The ratio of water to the water miscible, low boiling solvent may range from about 0:100 to about 99:1, from about 5:95 to about 95:1, to about 50:50. In other embodiments, the fibers may be contacted with a combination of a water-based solution and a water miscible, low boiling solvent prior to placement or after placement in the mold 4. The ratio of the water-based solution to the water miscible, low boiling solvent may range from about 0:100 to about 99:1, from about 5:95 to about 95:1, to about 50:50. In a preferred embodiment, the fibers 2 may be slurried in a solution containing a water miscible, low boiling solvent prior to placement within the mold 4. After the fibers are placed in the mold 4, a lid 3 may be placed on the mold 4 if desired. Excess moisture will be allowed to drain from the fibers within the mold 4.

The apparatus may be placed into a drying chamber 6 in a frozen or thawed state. The drying step may consist of blowing gas through the mold and/or subjecting the apparatus to reduced pressure, heating, lyophilization (under reduced pressure), or a combination of heating and vacuum. The gas used may include, but is not limited to, nitrogen, helium, argon, and combinations thereof. The drying may be performed under reduced pressure between about 1 nTorr and about 740 Torr. The drying step may consist of, or include, air flow into or through the mold. In some embodiments, the mold 4 or mold lid 3 may provide user-adjustable pressure to allow variance of the compaction of the resultant article. This user-adjustable pressure of the mold 4 or mold lid 3 may allow for articles of varied "sponginess" or flexibility. Drying may include heating the material to a temperature between about 30° C. to about 80° C., in some embodiments about 40° C. Following drying, the mold may be removed from the drying chamber 6, and the shaped product 1 may be removed from the mold. In some embodiments, the use of fibers 2 slurried in a solvent containing a water miscible, low boiling solvent prior to placement within the mold 4 results in an article with improved shape retention and with improved mold release characteristics.

In some embodiments, following forming of the bone fibers into the mold 4, the filled mold may be frozen at a temperature of about −100° C. to about 0° C., of about −90° C. to about −10° C. to about −80° C. to about −20° C. The apparatus may be placed into a drying chamber 6 in a frozen or thawed state. The drying step may include subjecting the apparatus to reduced pressure, heating, lyophilization (under reduced pressure), or a combination of dehydration and lyophilization. In preferred embodiments, the drying/lyophilization step is performed under reduced pressures of about 0.100 Torr to about 600 Torr, about 0.800 Torr to about 400 Torr, about 1.8 Torr to about 300 Torr, or any sub-range within the largest range. Drying may include heating the material to a temperature between about 30° C. to about 80° C., in some embodiments about 45° C. The temperature of the drying step may change over the time period of the drying from about 80° C. to −80° C., from about 60° C. to −70° C., from about 50° C. to 0° C., from about 45° C. to 25° C. Drying may take place over the range of about 1 hour to about 48 hours, of about 3 hours to about 30 hours, of about 4 hours to about 25 hours. During the drying step, the vacuum may be increased from an initial pressure of about 100 Torr to about 600 Torr, of about 200 Torr to about 400 Torr, of about 300 Torr; to a pressure of about 100 mTorr to about 30,000 mTorr, of about 800 mTorr to about 3000 mTorr, of about 1800 mTorr, or any other sub-range within the larger range. Following drying, the mold may be removed from the drying chamber 6, and the shaped product 1 may be removed from the mold. In some embodiments, the drying of fibers 2 within the mold 4 under the conditions described results in an article with improved shape retention and enhanced cohesiveness and flexibility upon rehydration. In the preferred embodiments, the drying of the fibers 2 within the mold 4 under the conditions described results in an article with retained osteoinductivity and a residual moisture content of less than about 6%, less than about 4%, or less than about 2%. In some embodiments, at least one rehydrated product property may be within about 60% to about 100% of its original property following rehydration. For example, the rehydrated product may be within about 75% of its initial shape, flexibility or compressibility prior to dehydration. In some embodiments, the rehydrated product may be within about 60%, about 65%, about 75%, about 85%, about 90%, about 95%, about 99% of its initial shape, the initial flexibility or the initial compressibility.

Table 1 illustrates several different drying protocols, each of which are suitable with the invention. All values provided in Table 1 are approximate.

TABLE 1

Drying protocols

| Step | Protocol 1 | Protocol 2 | Protocol 3 |
|---|---|---|---|
| Step 1 | 45° C., 300 torr, 300 min | 45° C., 300 torr, 300 min | 45° C., 300 torr, 300 min |
| Step 2 | 35° C., 300 torr, 900 min | 45° C. → 35° C., 300 torr, 900 min | 45° C. → 35° C., 300 torr, 720 min |
| Step 3 | 25° C., 300 torr until stopped | 25° C., 300 torr until stopped | 35° C., 2450 mtorr, 180 min |
| Step 4 | | | 25° C., 2450 mtorr, 10 min |
| Step 5 | | | 25° C., 2450 mtorr until stopped |

When bone fibers are demineralized and subjected to the lyophilization/drying conditions described in the existing art, the final shaped article fails to retain its shape, cohesiveness, pliability, and compressibility following rehydration within aqueous liquids of more than a few minutes or in some instances rehydration times of more than a few seconds, as illustrated in FIG. 3A. When the shaped, bone fiber-based products of the present invention are subjected to rehydration, the products retain their shape, cohesiveness, pliability, and compressibility. The products formed by the methods of the invention remain greater than about 90% intact upon rehydration in aqueous liquids. The products formed by the methods of the invention are bendable to greater than about 90° upon rehydration in aqueous liquids. The products formed by the methods of the invention display the highly desired properties of shape retention, cohesiveness, pliability, and compressibility upon rehydration for time periods of about 10 minutes to about 1 year, of about 1 hour to about 6 months, of about 3 hours to about 1 month. Suitable aqueous liquids for rehydration include, but are not limited to, water, salines, buffers, balanced salt solutions, blood, and bone marrow aspirate.

EXAMPLE

Example 1

A section of bovine cortical bone was shredded into fibers of an average length of about 15 mm and a average thickness of 1.0 mm using a bone shard cutter. The bone fibers were then demineralized following a modification version of the demineralization steps described in U.S. Pat. No. 5,314,476, which is incorporated in its entirety by reference. Briefly, the fibers were slurried in about 70 wt. % ethanol (about 30 mL/g of bone) for about one hour at room temperature. The ethanol was decanted off the fibers. Then about 0.6 N HCl was added to the fibers (about 15 mL/g of bone). The acid mixture was stirred for three hours at about room temperature. Following decanting of the acid, the fibers were covered and rinsed three times with water. The water for each rinse was replaced at about five-minute intervals. Following decanting of the final water rinse, the fibers were covered with about 0.1 M sodium phosphate and soaked at about room temperature until the pH of the solution was greater than about 6.8. Following decanting of the sodium phosphate solution, the fibers were rinsed two times with water. The water for each rinse was replaced at about five-minute intervals. The fibers were then split into two groups for comparison.

One group of the demineralized fibers were slurried in water for about five minutes at about room temperature and then placed directly in a mold and the excess water was allowed to drain from the mold. The mold containing the "untreated" fibers was then placed into an oven and held at about 40° C. for about eight hours.

The other group of demineralized fibers were slurried in 100% ethanol for about five minutes at about room temperature. The ethanol was decanted from the fibers and the fibers were placed in a mold. The excess liquid was allowed to drain from the mold. The mold containing the ethanol-treated fibers was then placed into an oven and held at about 40° C. for about eight hours.

Figure 3:
FIG. 3 illustrates an ethanol-treated shaped fiber-based product produced by an exemplary embodiment of the disclosed method and an untreated product retained within the shaping molds.
Figure 4:
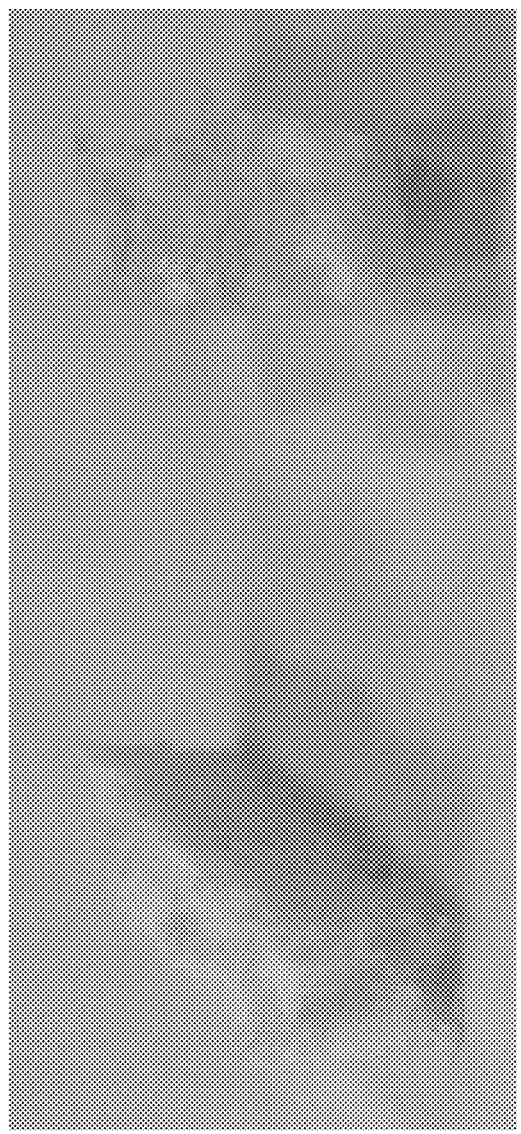
FIG. 4 illustrates an ethanol-treated shaped fiber-based product produced by an exemplary embodiment of the disclosed method and an untreated product.

After eight hours, the molds were removed from the oven. FIG. 3 illustrates the two samples within the molds. As illustrated in FIG. 3, the ethanol-treated product retained its shape during drying and began to partially release from the mold, facilitating removal of the product from the mold. The untreated product collapsed during drying and adhered to the underlying mold. FIG. 4 shows the two shaped fiber-based products released from the molds. As shown in FIG. 4, the ethanol-treated product retained the regular shape of the underlying mold more than the untreated product.

Example 2

A section of cortical bone was shredded into fibers of an average length of about 15 mm and an average thickness of about 1.0 mm using a bone shard cutter. The mineralized bone fibers were then demineralized following a modified version of the demineralization steps described in U.S. Pat. No. 5,314,476, which is incorporated in its entirety by reference. Following acid demineralization and neutralization of the acid, the moisture-saturated fibers were poured into perforated metal molds. The excess liquid was allowed to drain out of the molds The fiber-containing molds were split into two groups for comparison. Each group of molds were subjected to two drying/lyophilization conditions (see Table 2 below for drying/lyophilization conditions). All of the values given in Table 2 are approximate.

TABLE 2

| Drying/Lyophilization Conditions | | | | | |
|---|---|---|---|---|---|
| Group A Products | | | Group B Products | | |
| Shelf Temperature (° C.) | Time (minutes) | Vacuum Pressure | Shelf Temperature (° C.) | Time (minutes) | Vacuum Pressure |
| −60 | 30 | 200 mT | 45 | 300 | 300 Torr |
| 37 | 1080 | 50 mT | 35 | 900 | 300 Torr |

Figure 5A:
FIG. 5A illustrates a rehydrated product produced by methods known in the prior art.
Figure 5B:
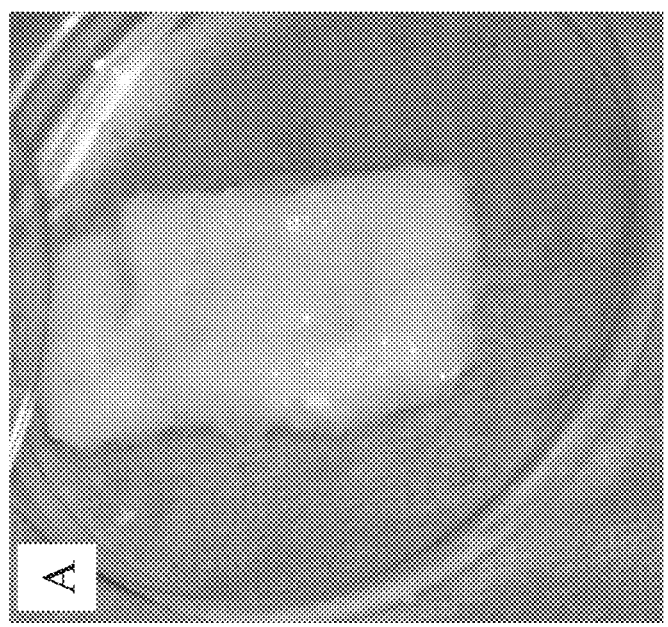
FIG. 5B illustrates a rehydrated product produced by an exemplary embodiment of the disclosed method.

After treatment to the conditions detailed in Table 2, the shaped, bone fiber-based products were removed from the molds. Both drying/lyophilization conditions provided products that were shaped by the molds. However, upon rehydration in saline for less than ten minutes, the bone fibers of the Group A products began to completely dissociate (see FIG. 5A). The Group B products remained >90% intact, pliable, and compressible for greater than one week in the fully hydrated state (see FIG. 5B).

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A shaped, dehydrated bone fiber-based product, comprising:
   a plurality of at least partially demineralized bone fibers comprising at least one native growth factor selected from the group consisting of:
   IGF-1 in an amount greater than 60 pg per gram of demineralized bone matrix,
   BMP-2 in an amount greater than 2700 pg per gram of demineralized bone matrix,
   BMP-4 in an amount greater than 200 pg per gram of demineralized bone matrix,
   BMP-7 in an amount greater than 9000 pg per gram of demineralized bone matrix,
   and combinations thereof,
   and having an average length between about 1 and about 200 mm and a void to fiber ratio of between about 1:99 to about 1:11,
   wherein the dehydrated bone fiber-based product, upon rehydration, is within about 60% to about 100% of at least one of a pre-dehydrated shape, a pre-dehydrated flexibility, and a pre-dehydrated compressibility.

2. The shaped, dehydrated bone fiber-based product of claim 1, wherein the shape is selected from the group consisting of a cube, a block, a strip, and a sphere.

3. The shaped, dehydrated bone fiber-based product of claim 1, wherein the plurality of at least partially demineralized bone fibers are selected from the group consisting of cortical bone, cancellous bone, and combinations thereof.

4. The shaped, dehydrated bone fiber-based product of claim 1, wherein the plurality of at least partially demineralized bone fibers are a fully demineralized bone.

5. The shaped, dehydrated bone fiber-based product of claim 1, wherein the plurality of at least partially demineralized bone fibers have a diameter between about 0.1 mm to about 30 mm.

6. The shaped, dehydrated bone fiber-based product of claim 1, wherein the plurality of at least partially demineralized bone fibers are selected from the group comprising allogeneic tissues, autogeneic tissues, xenogeneic tissues, and combinations thereof.

7. The shaped, dehydrated bone fiber-based product of claim 1, wherein the plurality of at least partially demineralized bone fibers are cut from a bone in a direction about 15° to about 90° from the grain of native collagen fibers.

8. The shaped, dehydrated bone fiber-based product of claim 1, wherein a residual moisture content of the dehydrated bone fiber-based product is less than about 6%.

9. The shaped, dehydrated bone fiber-based product of claim 1, wherein the dehydrated bone fiber-based product, upon rehydration, is bendable to about 90°.

10. The shaped, dehydrated bone fiber-based product of claim 1, wherein the dehydrated bone fiber-based product, upon rehydration, is osteoinductive.

11. The shaped, dehydrated bone fiber-based product of claim 1, wherein the void to fiber ratio is between about 1:19 and about 1:3.

12. The shaped, dehydrated bone fiber-based product of claim 1, wherein the bone fiber-based product, upon rehydration, remains greater than about 90% intact compared to an intact percentage of the hydrated bone fiber-based product.

13. The shaped, dehydrated bone fiber-based product of claim 1, wherein the dehydrated bone fiber-based product, upon rehydration, remains greater than about 90% intact after it is bent, compressed, twisted, squeezed, or rolled.

14. The shaped, dehydrated bone fiber-based product of claim 1, wherein, upon rehydration, the bone fiber-based product compresses under a force of between about 10 g-force/square cm to about 4000 g-force/square cm.

15. The shaped, dehydrated bone fiber-based product of claim 1, wherein the shaped dehydrated bone fiber-based product, upon rehydration, is not a putty.

16. A three-dimensionally shaped, fiber-based product, comprising:
a plurality of at least partially demineralized bone fibers having an average length of about 1 mm to about 200 mm and comprising at least one native growth factor selected from the group consisting of:
IGF-1 in an amount greater than 60 pg per gram of demineralized bone matrix,
BMP-2 in an amount greater than 2700 pg per gram of demineralized bone matrix,
BMP-4 in an amount greater than 200 pg per gram of demineralized,
BMP-7 in an amount greater than 9000 pg per gram of demineralized bone matrix,
and combinations thereof; and
a plurality of fibers of a second material selected from the group consisting of wood, food stuffs, plant-based materials, elastomers, thermoplastics, and combinations thereof,
wherein the fiber-based product comprises a void to fiber ratio of between about 1:99 to about 1:11.

17. The product of claim 16, which has a width between about 1 mm and about 5 mm, and a thickness between about 0.01 mm and about 1 mm.

18. The product of claim 16, wherein the at least partially demineralized bone is a cortical bone.

* * * * *